US011535886B2

(12) United States Patent
Schmidt et al.

(10) Patent No.: US 11,535,886 B2
(45) Date of Patent: Dec. 27, 2022

(54) ARRAY-BASED METHODS FOR ANALYSING MIXED SAMPLES USING DIFFERENT ALLELE-SPECIFIC LABELS, IN PARTICULAR FOR DETECTION OF FETAL ANEUPLOIDIES

(71) Applicant: AFFYMETRIX, INC., Carlsbad, CA (US)

(72) Inventors: Jeanette Schmidt, Palo Alto, CA (US); Orna Mizrahi Man, Amirim, IL (US); Jiang Li, Fremont, CA (US)

( * ) Notice: Subject to any disclaimer, the term of this patent is extended or adjusted under 35 U.S.C. 154(b) by 274 days.

(21) Appl. No.: 16/616,725

(22) PCT Filed: Jun. 1, 2018

(86) PCT No.: PCT/US2018/035688
§ 371 (c)(1),
(2) Date: Nov. 25, 2019

(87) PCT Pub. No.: WO2018/223057
PCT Pub. Date: Dec. 6, 2018

(65) Prior Publication Data
US 2021/0147918 A1    May 20, 2021

Related U.S. Application Data (60) Provisional application No. 62/514,681, filed on Jun. 2, 2017.

(51) Int. Cl.
*C12Q 1/6827* (2018.01)
*C12Q 1/6837* (2018.01)

(52) U.S. Cl.
CPC ......... *C12Q 1/6827* (2013.01); *C12Q 1/6837* (2013.01); *C12Q 2535/131* (2013.01); *C12Q 2537/125* (2013.01); *C12Q 2537/143* (2013.01)

(58) Field of Classification Search
CPC ................. C12Q 2535/131; C12Q 1/6837
See application file for complete search history.

(56) References Cited

U.S. PATENT DOCUMENTS

| 6,534,293 B1 | 3/2003 | Barany et al. |
| 2011/0029251 A1 | 2/2011 | Huang et al. |
| 2013/0059733 A1* | 3/2013 | Lo ........................ C12Q 1/6881 506/2 |

FOREIGN PATENT DOCUMENTS

| WO | WO-2007147079 A2 | 12/2007 |
| WO | WO-2015154028 A1 | 10/2015 |
| WO | WO-2016018986 A1 | 2/2016 |
| WO | WO-2017020023 A2 | 2/2017 |
| WO | WO-2017205827 A1 | 11/2017 |

OTHER PUBLICATIONS

Juneau, K. et al., Microarray-Based Cell-Free DNA Analysis Improves Noninvasive Prenatal Testing, Fetal Diagnosis and Therapy, vol. 36, pp. 282-286 (Year: 2014).*
Affymetrix Genotyping Console 4.0, User Manual, pp. 1-327 (Year: 2009).*
Affymetrix white paper"DMET Plus Genotyping and copy number methods", pp. 1-29 (Year: 2011).*
Huang, M-C. et al., An integrated analysis tool for analyzing hybridization intensities and genotypes using new-generation population-optimized human arrays, BMC Genomics, vol. 17:266, pp. 1-30 (Year: 2016).*
Fan J-B, et al., "Highly Parallel SNP Genotyping," Cold Spring Harbor Symposia on Quantitative Biology, vol. 68, Jan. 1, 2003 (Jan. 1, 2003), pp. 69-78, XP001538040, DOI: 10.1101/SQB.2003.68.69.
Gunderson K.L, et al., "A Genome-Wide Scalable SNP Genotyping Assay Using Microarray Technology," Nature Genetics, vol. 37, No. 5, May 1, 2005 (May 1, 2005), pp. 549-554, XP002561532, DOI: 10.1038/NG1547.
Nicolaides K.H, et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, vol. 33, No. 6, Jun. 24, 2013 (Jun. 24, 2013), pp. 575-579, XP055257233, DOI: 10.1002/pd.4103.
PCT/US2018/035684, Preliminary Reporton Patentability, dated Dec. 12, 2019.
PCT/US2018/035684, Search Report and Written Opinion, dated Aug. 3, 2018, 12 pages.
PCT/US2018/035686, Preliminary Reporton Patentability, dated Dec. 12, 2019.
PCT/US2018/035686, Search Report and Written Opinion, dated Aug. 3, 2018, 13 pages.
PCT/US2018/035688, Preliminary Reporton Patentability, dated Dec. 12, 2019.
PCT/US2018/035688, Search Report and Written Opinion, dated Aug. 2, 2018, 10 pages.
Zhang H, et al., "Statistical Approach to Decreasing the Error Rate of Noninvasive Prenatal Aneuploid Detection Caused by Maternal Copy Number Variation", Scientific Reports, vol. 5, No. 1, Nov. 4, 2015 (Nov. 4, 2015), pp. 1-9, XP055407852, DOI: 10.1038/srep16106.
Attiyeh E.F., et al., "Genomic Copy Number Determination in Cancer Cells From Single Nucleotide Polymorphism Microarrays Based on Quantitative Genotyping Corrected for Aneuploidy," Genome Research, 2009, vol. 19, pp. 276-283.

(Continued)

*Primary Examiner* — Teresa E Strzelecka
(74) *Attorney, Agent, or Firm* — Workman Nydegger; Logan Christenson; John Guynn (57) ABSTRACT

Provided includes methods and systems useful in array-based analysis of mixed nucleic acid populations, including for genotyping and copy number analysis of the various subpopulations of the mixed nucleic acid population. Also provided includes methods and systems useful in the diagnosis of genetic abnormalities in a mixed nucleic acid population taken from an organism.

16 Claims, 6 Drawing Sheets

(56) References Cited

OTHER PUBLICATIONS

Wang, et al. (2009) "High quality copy number and genotype data from FFPE samples using Molecular Inversion Probe (MIP) microarrays." BMC Med Genomics, 2(8):1-13.

* cited by examiner

ARRAY-BASED METHODS FOR ANALYSING MIXED SAMPLES USING DIFFERENT ALLELE-SPECIFIC LABELS, IN PARTICULAR FOR DETECTION OF FETAL ANEUPLOIDIES

RELATED APPLICATIONS

This application is a U.S. 371 patent application of International Application No. PCT/US2018/035688 filed Jun. 1, 2018, which claims priority to U.S. Provisional Application No. 62/514,681 filed Jun. 2, 2017, all of which disclosures are herein incorporated by reference in their entirety.

BACKGROUND

This disclosure provides methods and systems useful in array-based analysis of mixed nucleic acid populations, including for genotyping and copy number analysis of the various subpopulations of the mixed nucleic acid population. The disclosure also provides methods and systems useful in the diagnosis of genetic abnormalities in a mixed nucleic acid population taken from an organism. For example, disclosed herein are methods and systems useful in the diagnosis of fetal genetic abnormalities or tumor genetic abnormalities using samples obtained noninvasively from pregnant females or patients. Such samples can include mixed nucleic acid populations derived from blood, plasma, serum, urine, stool or saliva.

Analysis of mixed nucleic acid populations, for example DNA and RNA samples obtained from a single tissue source such as blood, urine or saliva but containing distinct nucleic acid subpopulations, has elicited significant interest in the research and health care communities. Using suitable methods, mixed nucleic acid populations derived from cell-free DNA (or RNA) taken from pregnant females can be analyzed to determine fetal characteristics, including disease inheritance. Similarly, mixed nucleic acid populations derived from cell-free DNA (or RNA) taken from cancer patients can be analyzed to determine various characteristics such as tumor malignancy, tumor origin or drug susceptibility. While analysis of such mixed nucleic acid populations can be technically complex due to the high degree of similarity between the various subpopulations, the difficulty of the analysis is outweighed by the ease of obtaining appropriate nucleic acid samples cheaply, quickly and non-invasively through procedures such as phlebotomy or urine/saliva collection. One mode of analyzing cell-free DNA, nucleic acid sequencing, is informative but costly on a per-sample and time-consuming. Microarray analysis is cheaper and quicker than sequencing, but current commercial embodiments of microarray products do not readily support discrimination between the different and highly similar subpopulations present in a mixed nucleic acid population. As a result of the low concentration of fetal DNA in maternal samples, and low concentration of tumor DNA in a blood sample containing circulating tumor cells, single or low multiplex assays are unlikely to differentiate between an aneuploid fetus (e.g., trisomy of chromosome 21) from a euploid fetus, or a tumor cell from a healthy cell in a cancer patient. For example, fetal DNA can be present at levels of between 4%-15% of total cell-free DNA in blood; DNA derived from a particular fetal chromosome would represent one-twenty-third of such fetal DNA. Detection of a trisomy would require reliable detection of signal changes as low as 1-2% above background. Moreover, the analysis is further complicated by the limited amount of nucleic acid available through non-invasive sampling methods. For example, a maternal sample of 10 mls of whole blood can yield between 5 and 15 ng of purified cell-free DNA in a typical assay.

Due to the current challenges posed by such non-invasive approaches, a majority of pregnant women are subject to prenatal testing, including maternal serum screening and/or an ultrasound test, to determine risks for common birth defects, such as those resulting from trisomy 13, 18, and 21. However, the sensitivity and specificity of such tests are very poor leading to high false positive rates. As a result of the high false positive rates of such conventional tests, individuals typically must conduct follow-up testing with an invasive diagnostic test, such as Chorionic Villus Sampling (CVS) between 11 and 14 weeks gestation or amniocentesis after 15 weeks gestation. These invasive procedures carry a risk of a miscarriage of around one percent (see Mujezinovic and Alfirevic, Obstet. Gynecol., 110:687-694 (2011)). Current analysis of fetal cells typically involves karyotyping or fluorescent in situ hybridization (FISH) and does not provide information about single gene traits. As a result, additional tests are required for identification of single gene diseases and disorders. Because prenatal diagnosis can be critical for management of a pregnancy with chromosomal abnormalities and localized genetic abnormalities, an accurate and early diagnosis is important to allow for interventional care before or during delivery and to prevent devastating consequences for the neonate.

Similarly, on the cancer front, powerful tools such as OncoScan® have been developed for purposes of diagnosing cancers. However, such samples are typically biopsy samples taken in invasive procedures that are both expensive and potentially risky to the patient. Through the use of microarray-based technology, researchers are able to identify large numbers of Single Nucleotide Polymorphisms (SNPs) on a single array, which allows for the rapid and accurate detection of genetic abnormalities in a subject. As an example of one such product is the SNP detection microarray product from Affymetrix called OncoScan®. The OncoScan® product provides genome-wide copy number and loss-of-heterozygosity (LOH) profiles from solid tumor samples. Such a technology is a powerful tool in cancer diagnostics because it helps to overcome significant challenge due to the difficulty of working with limited amounts of DNA from highly degraded FFPE samples. See, for example, U.S. Pat. No. 8,190,373. However, such technologies are finding application in numerous other fields, as well. Specifically, genetic abnormalities account for a wide number of pathologies, including pathologies caused by chromosomal aneuploidy (e.g., Down syndrome), germline mutations in specific genes (e.g., sickle cell anemia), and pathologies caused by somatic mutations (e.g., cancer), and in many cases, the detection of such genetic abnormalities is complicated by invasive diagnostic procedures.

As such, the development of a microarray based test that is sensitive and specific enough to detect genetic abnormalities in samples obtained by non-invasive means with low false-positive and false-negative rates would be of benefit to the field of molecular diagnostics. Recently, Ariosa Diagnostics reported studies involving microarray based analysis of cell-free DNA from maternal blood to detect the presence of fetal aneuploidies. See, e.g., Stokowski et al., Prenatal Diagnosis 35:1243-1246 (2015). Such methods involved analysis of bulk signals from non-polymorphic loci (i.e., loci that are expected to be identical for both mother and fetus) to estimate chromosomal copy number by measuring fluctuations in total signal detected from both maternal and fetal DNA at a given genetic locus. This necessitates a design strategy whereby the array is configured to interrogate non-polymorphic loci to determine copy number of the underlying chromosomes.

Furthermore, at least in some cases use of polymorphic loci for estimating copy numbers has downstream benefits in the context of testing for fetal aneuploidy because it preserves the possibility of determining which parent contributed to the copy number variation. However, copy number analysis based on signals corresponding to polymorphic sites can be challenging and these challenges are magnified when analyzing samples from different populations.

There is a need to develop improved methods (as all as associated compositions, systems, devices and instruments) that leverages the high-throughput genotyping capabilities of microarray-based analysis to generate data from a single set of interrogation sites (for example, a data from a single set of polymorphic loci in mixed DNA populations), which can then be used to both genotype and estimate copy number of a given locus or chromosome within the major and minor DNA populations within mixed nucleic acid populations.

Described herein are methods and systems for analyzing a mixed nucleic acid sample to detect differences in copy number of a target polynucleotide, such as a detection of copy number variants indicating chromosomal aneuploidy, as well as methods of genotyping such target polynucleotides even when present at low levels within a mixed nucleic acid population.

SUMMARY

One embodiment of the invention, in the context of a probe array, uses signals associated with first and second nucleotide variants present in a nucleic acid sample from an organism to measure copy numbers, the nucleic acid sample containing a mixed nucleic acid population. In one embodiment, copy numbers (for example, of a chromosome and/or of a chromosomal region and/or of a particular nucleotide sequence) are measured (e.g., estimated) with respect to a minor subpopulation within the mixed nucleic acid population of the nucleic acid sample. In one embodiment, the nucleic acid sample is obtained from a pregnant mother and contains a major nucleic acid subpopulation corresponding to DNA of the mother and a minor subpopulation corresponding to fetal DNA. In another embodiment, the nucleic acid sample is obtained from an individual with cancer or other tumors and the major nucleic acid subpopulation corresponds to DNA from non-tumor cells and the minor subpopulation corresponds to DNA from tumor cells. Some embodiments of the invention are also applicable to various other contexts in which measurement of copy numbers is desired for a nucleic acid sample containing a mixed nucleic acid population including at least a major subpopulation and a minor subpopulation.

In a particular embodiment of the invention, signals corresponding to probes hybridized to nucleotide variants associated with polymorphic sites are used to measure copy numbers of a minor subpopulation of a mixed nucleic acid population in a nucleic acid sample obtained from an organism.

In some alternative embodiments, a probe array comprises a plurality of probes for polymorphic sites usable for measuring potential copy number variations in samples and signals from a pre-selected subset of the plurality of probes are used to estimate fetal fraction (or, in other embodiments, the fraction of another type of subpopulation associated with a sample), the preselected subset of probes having been selected based on performance of the probes with a model used to predict allele frequency from signal values.

In some embodiments of the invention, reference signal values that are genotype specific for a polymorphic locus are used for detecting copy number variations.

Certain aspects and various embodiments of the disclosure can be further described by the following enumerated clauses:

1. A method for detecting a copy number in a fetus, comprising: obtaining a biological sample from a subject who is a pregnant female, the biological sample including nucleic acid of both maternal and fetal origin containing a target nucleic acid sequence located on a first chromosome, the target nucleic acid sequence containing a polymorphic site for a single nucleotide polymorphism (SNP); generating a population of nucleic acid fragments containing or derived from the target nucleic acid sequence; conducting a first assay comprising (a) contacting the population of nucleic acid fragments with an oligonucleotide array containing a first oligonucleotide probe configured to hybridize to the target nucleic acid sequence containing the polymorphic site of the SNP; and (b) detecting, using a detector, first signals indicating hybridization of the oligonucleotide probe to one or more nucleic acid fragments of the population containing a first allelic variant ("A allele") of the SNP and second signals indicating hybridization of the oligonucleotide probe to one or more nucleic acid fragments of the population containing a second allelic variant ("B allele") of the SNP; and determining, using the first signals and the second signals, any one or more of the following: (i) the copy number of the first chromosome in the fetus; (ii) a fetal genotype for the SNP; (iii) a maternal genotype for the SNP; and (iv) a fetal fraction of the sample.

2. The method of clause 1, further comprising calculating the observed B-allele frequency (BAF) for the allelic variants of the SNP present in the sample.

3. The method of clause 2, further including calculating the fetal fraction of the sample using the BAF.

4. The method of clause 1, wherein the polymorphic site of the SNP can be homozygous for the A allele ("AA"), homozygous for the B allele ("BB") or heterozygous ("AB").

5. The method of clause 4, wherein the detector has a first and a second detection channel, and the genotyping further includes detecting the first signals in the first channel and the second signals in the second channel.

6. The method of clause 5, wherein the first signals in the first channel indicate the amount of A allele present in the nucleic acid population and the second signals indicate the amount of B allele present at nucleic acid population.

7. The method of clause 6, wherein determining the copy number of the first chromosome in the fetus comprises determining a ratio of a first value to a second value.

8. The method of clause 7, further comprising calculating the first value by normalizing and summarizing the first signals to obtain a first normalized and summarized signal value, normalizing the second signals to obtain a normalized and summarized second signal value, and adding the normalized and summarized first signal value to normalized and summarized second signal value to obtain the first value.

9. The method of clause 4, further including determining a first maternal SNP genotype.

10. The method of clause 8, wherein the second value is obtained by: conducting the first assay on additional biological samples serving as reference samples and identifying reference samples having an SNP genotype corresponding to the first maternal SNP genotype; from conducting the first assay on the reference samples, obtaining first signals reference signals detected in the first channel indicating an amount of A allele present in the polymorphic site of the SNP with respect to the additional biological samples and obtaining second reference signals indicating the amount of B allele present at the polymorphic site.

11. The method of clause 10 wherein the additional biological samples are from non-pregnant individuals.

12. The method of clause 10 wherein the additional biological samples include some samples from pregnant females and some samples from non-pregnant individuals.

13. The method of clause 10 wherein the additional biological samples include samples from pregnant females assayed on the same oligonucleotide array as the biological sample from the subject pregnant female.

14. The method of clause 1, wherein the nucleic acid sample includes maternal blood, plasma or serum and the nucleic acid of both maternal and fetal origin includes cell-free DNA (cfDNA).

15. The method of clause 1, wherein the fetal DNA is about 30% of total DNA in the nucleic acid sample.

16. The method of clause 1, wherein the fetal DNA is no greater than 30% of total DNA in the nucleic acid sample.

17. The method of clause 1, wherein the fetal DNA is more than 30% of total DNA in the nucleic acid sample.

18. The method of clause 1, wherein the fetal DNA is no greater than 20% of total DNA in the nucleic acid sample.

19. The method of clause 1, wherein the fetal DNA is no greater than 15% of total DNA in the nucleic acid sample.

20. The method of clause 1, wherein the fetal DNA is no greater than 10% of total DNA in the nucleic acid sample.

21. The method of clause 1, wherein the fetal DNA is no greater than 5% of total DNA in the nucleic acid sample.

22. The method of clause 1, wherein the fetal DNA is no greater than 15% and no less than 1% of total cell free DNA in the nucleic acid sample.

23. The method of clause 1, wherein the fetal DNA is no less than 30% of total cell free DNA in the nucleic acid sample.

24. A method for analyzing a mixed nucleic acid sample obtained from an organism, comprising: obtaining or deriving from an organism a nucleic acid sample containing a mixed nucleic acid population that includes a major subpopulation and a minor subpopulation, the major and minor subpopulations each including a target sequence located in a first chromosomal region and containing a polymorphic site, wherein the polymorphic site can include any combination of a first nucleotide variant and a second nucleotide variant; genotyping the polymorphic site, wherein the genotyping includes: (a) hybridizing at least one nucleic acid fragment derived from the mixed nucleic acid population and containing the polymorphic site to an oligonucleotide probe of an oligonucleotide array; and (b) detecting from the oligonucleotide array, using a detector, a first signal indicating the presence or absence of the first nucleotide variant ("A signal") and a second signal indicating the presence or absence of the second nucleotide variant ("B signal").

25. The method of clause 24, further including determining the copy number of the first chromosomal region in the minor subpopulation using the first signal and the second signal.

26. The method of clause 24, further including determining the copy number of the first chromosomal region in the major subpopulation using the first signal and the second signal.

27. The method of clause 24, further including determining the genotype of the polymorphic site for the minor subpopulation using the first signal and the second signal.

28. The method of clause 24, further including determining the genotype of the polymorphic site for the major subpopulation using the first signal and the second signal.

29. The method of clause 24, further including determining the relative amounts of the major subpopulation and the minor subpopulation in the mixed nucleic acid population using the first signal and the second signal.

30. The method of any of the preceding clauses, wherein the major subpopulation and the minor subpopulation original from different sources in the organism.

31. The method of clause 24, wherein the detector includes a first detection channel and a second detection channel, and further including the steps of detecting the first signal in the first detection channel and the second signal in the second detection channel.

32. The method of any of the preceding clauses, wherein the mixed nucleic acid population includes cell-free DNA.

33. The method of clause 30, wherein the cell-free DNA is obtained or derived from the organism's blood, plasma, serum, urine, stool or saliva.

34. The method of any of the preceding clauses, wherein the organism includes a tumor, the major subpopulation includes or is derived from normal tissue and the minor subpopulation includes or is derived from the tumor.

35. The method of any of the preceding clauses, wherein the organism is a pregnant female, the mixed nucleic acid population is cell-free nucleic acid obtained from the female's blood, the major subpopulation is maternal nucleic acid and the minor subpopulation includes or is derived from fetal nucleic acid.

36. The method of clause 35, wherein the minor subpopulation includes fetal DNA present at no greater than 40% of total DNA in the nucleic acid sample.

37. The method of clause 35, wherein the fetal DNA is no greater than 25% of total DNA in the nucleic acid sample.

38. The method of clause 35, wherein the fetal DNA is no greater than 15% of total DNA in the nucleic acid sample.

39. The method of clause 35, wherein the fetal DNA is no greater than 5% of total DNA in the nucleic acid sample.

40. The method of clause 35, wherein the fetal DNA is no greater than 15% and no less than 1% of total cell free DNA in the nucleic acid sample.

41. The method of any of the preceding clauses, wherein the mixed nucleic acid population contains or is derived from cell-free DNA present in blood of the organism at concentration of no greater than 5 ng/ml and no less than 0.1 ng/ml.

42. The method of clause 24, wherein the amount of mixed nucleic acid population used is no greater than 50 ngs, 40 ngs, 30 ngs, 15 ngs, 10 ngs, 5 ngs, 3 ngs or 1 ng.

43. The method of clause 24 or 35, wherein the polymorphic site includes a bi-allelic SNP, the first nucleotide variant is a first allelic variant of the SNP ("A allele") and the second nucleotide variant is a second allelic variant of the SNP ("B allele").

44. The method of clause 43, wherein the bi-allelic SNP that can include one or both of the first allelic variant ("A allele") or the second allelic variant ("B allele"), and wherein the SNP genotype can be homozygous for the A allele ("AA"), homozygous for the B allele ("BB") or heterozygous ("AB").

45. The method of clause 43, further including calculating the observed B-allele frequency (BAF) for the SNP in the nucleic acid sample.

46. The method of clause 45, further including calculating the fetal fraction of the sample using the BAF.

47. The method of clause 24 or 35, wherein the first signal indicates the amount of A allele present in the polymorphic site and the second signal indicates the amount of B allele present at the polymorphic site.

48. The method of clause 24, 35 or 47, wherein the organism is a pregnant female, and wherein the method further includes determining the copy number of the first chromosomal region in the fetus by determining a ratio of a first value to a second value.

49. The method of clause 48, further including calculating the first value by adding the first signal, or a normalized value thereof, and the second signal, or a normalized value thereof.

50. The method of clause 49, further including determining a first maternal SNP genotype using the first signal and the second signal.

51. The method including performing the method of clause 46 using one or more additional biological samples from pregnant females and identifying a subset of additional biological samples having a SNP genotype corresponding to the first maternal SNP genotype, and obtaining a second value by taking sums of the A signal and the B signal from each additional sample in the subset of additional biological samples and obtaining a medium of the sums as the second value.

52. The method of clause 24, 34 or 35, wherein the polymorphic site includes a nucleotide mutation, the first nucleotide variant is the mutant version of the target nucleic acid sequence and the second nucleotide variant is the wild-type version of the polymorphic site, the A signal indicates the amount of the mutant version and the B signal indicates the amount of wild-type version in the sample.

53. A system for use in detecting copy number variation in a nucleic acid sample, the system comprising: a probe microarray; a scanner; a processor; and a memory encoded with instructions for carrying out processing referenced in any one of clauses 1-52 above.

54. A computer program product in a non-transitory computer readable medium storing instructions for carrying out processing referenced in any one of clauses 1-53 above.

These and other various embodiments are disclosed in further detail below and in the accompanying drawings.

While the invention is described with reference to the above drawings, the drawings are intended to be illustrative, and other embodiments are consistent with the spirit, and within the scope, of the invention.

DETAILED DESCRIPTION

The various embodiments now will be described more fully hereinafter with reference to the accompanying drawings, which form a part hereof, and which show, by way of illustration, specific examples of practicing the embodiments. This specification may, however, be embodied in many different forms and should not be construed as limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

As used in this application, the singular form "a," "an," and "the" include plural references unless the context clearly dictates otherwise. For example, the term "an agent" includes a plurality of agents, including mixtures thereof.

All references cited herein are incorporated herein in their entireties for all their purposes. To the extent any reference includes a definition or uses a claim term in a manner inconsistent with the definitions and disclosure set forth herein, the definitions and disclosure of this application will control.

Disclosed herein are methods (as well as associated systems, apparatuses and software) for performing array-based analysis of mixed nucleic acid populations. The array or microarray optionally comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800, 992, 6,040,193, 5,424,186 and Fodor et al., Science, 251: 767-777 (1991). Each of which is incorporated by reference in its entirety for all purposes. The probes can be of any size or sequence, and can include synthetic nucleic acids, as well as analogs or derivatives or modifications thereof, as long as the resulting array is capable of hybridizing under any suitable conditions with a nucleic acid sample with sufficient specificity as to discriminate between different target nucleic acid sequences of the sample. In some embodiments, the probes of the array are at least 5, 10 or 20 nucleotides long. In some embodiments, the probes are no longer than 25, 30, 50, 75, 100, 150, 200 or 500 nucleotides long. For example, the probes can be between 10 and 100 nucleotides in length.

In some embodiments, the array is capable of genotyping nucleic acid molecules in the mixed nucleic acid population. In some embodiments, to the determination of the nucleic acid sequence information from a nucleic acid sample at one or more nucleotide positions. The nucleic acid sample may contain or be derived from any suitable source, including the genome or the transcriptome. In some embodiments, genotyping may comprise the determination of which allele or alleles an individual carries at one or more polymorphic sites. For example, genotyping may include or the determination of which allele or alleles an individual carries for one or more SNPs within a set of polymorphic sites. For example, a particular nucleotide in a genome may be an A in some individuals and a C in other individuals. Those individuals who have an A at the position have the A allele and those who have a C have the B allele. In a diploid organism the individual will have two copies of the sequence containing the polymorphic position so the individual may have an A allele and a B allele or alternatively two copies of the A allele or two copies of the B allele. Those individuals who have two copies of the B allele are homozygous for the B allele, those individuals who have two copies of the A allele are homozygous for the B allele, and those individuals who have one copy of each allele are heterozygous. The array may be designed to distinguish between each of these three possible outcomes. A polymorphic location may have two or more possible alleles and the array may be designed to distinguish between all possible combinations. In some embodiments, genotyping includes detecting a single nucleotide mutation that arises spontaneously in the genome, amongst a background of wild-type nucleic acid. In some embodiments, genotyping includes determining fetal blood type from a sample of maternal blood or diagnosing cancer from a sample of human or animal blood.

A polymorphism can occur when there exist two or more genetically determined alternative sequences in a population. The alternative sequences can include alleles (e.g., naturally occurring variants) or spontaneously arising mutations that only occur in one or few individual organisms. A polymorphic site is formed by nucleic acid position(s) at which a difference in nucleic acid sequence occurs. A polymorphism may comprise one or more base changes, an insertion, a repeat, or a deletion. A polymorphic locus may be as small as one base pair. Polymorphic sites include restriction fragment length polymorphisms, variable number of tandem repeats (VNTR's), hypervariable regions, mini-satellites, dinucleotide repeats, trinucleotide repeats, tetra-nucleotide repeats, simple sequence repeats, and insertion elements. The first identified variant or allelic form is arbitrarily designated as the reference form and other variant or allelic forms are designated as alternative or variant or mutant alleles. The variant or allelic form occurring most frequently in a selected nucleic acid population is sometimes referred to as the wildtype form. In some embodiments, the wildtype form can be referred to as a "major subpopulation" and the mutant can be referred to as ta "minor subpopulation". In some embodiments, the more frequently occurring allele can be referred to as a "major subpopulation" and the rarer or less frequently occurring allele can be referred to as ta "minor subpopulation". Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. SNPs are positions at which two alternative bases occur at appreciable frequency (>1%) in the human population, and are the most common type of human genetic variation.

The following passages describe various embodiments of methods to analyze mixed nucleic acid populations and to determine the genotype and/or copy number of specific genetic loci present within different subpopulations (e.g., major and minor subpopulations) of the mixed nucleic acid population.

In some embodiments, a sample includes a mixed nucleic acid population from different subpopulations (e.g., major and minor subpopulations). In one embodiment, a sample contains a mixture of maternal nucleic acids (a major subpopulation) and fetal nucleic acids (a minor subpopulation.) In one embodiments, the nucleic acids from each subpopulation are cell-free DNA. In some embodiments, the amount of the fetal DNA in a sample ranges from about 1% to about 50% of the total amount of DNA in the sample. In some embodiments, the amount of the fetal DNA in the sample is about 1%, about 5%, about 10%, about 15%, about 20%, about 25%, about 30%, about 35%, about 40%, about 45% or about 50% of the total amount of DNA in the sample, or any intervening amount of the foregoing. In some embodiments, the amount of the fetal DNA in the sample is no greater than about 1%, about 5%, about 10%, about 15%, about 20%, about 25%, about 30%, about 35%, about 40%, about 45% or about 50% of the total amount of DNA in the sample, or any intervening amount of the foregoing. In some embodiments, the amount of the fetal DNA in the sample is more or no less than about 1%, about 5%, about 10%, about 15%, about 20%, about 25%, about 30%, about 35%, about 40%, about 45% or about 50% of the total amount of DNA in the sample, or any intervening amount of the foregoing.

In some embodiments, the mixed nucleic acid population in a sample that can be processed according to various methods disclosed herein includes cell-free DNA from major and minor sources. In some embodiments, the mixed nucleic acid population is circulating DNA isolated from whole blood, plasma, serum or some other bodily fluid. In some embodiments, the mixed nucleic acid population includes maternal and fetal cell-free DNA. In some embodiments, the amount of mixed nucleic acid population in a sample is in the range from one or more nanograms (ngs) to about one or more milligrams (mgs). In some embodiments, the amount mixed nucleic acid population is about 1 ng, about 3 ngs, about 5 ngs, about 10 ngs, about 15 ngs, about 30 ngs, about 40 ngs, about 50 ngs, about 100 ngs, about 150 ngs, about 300 ngs, about 400 ngs, about 500 ngs, about 1 mg, about 3 mgs, about 5 mgs or more, or any intervening amount of the foregoing. In some embodiments, the amount of the mixed nucleic acid population used is no greater than about 50 ngs, about 40 ngs, about 30 ngs, about 15 ngs, about 10 ngs, about 5 ngs, about 3 ngs or about 1 ng. In some embodiments, the amount mixed nucleic acid population is about or less than about 50 ngs, about 40 ngs, about 30 ngs, about 15 ngs, about 10 ngs, about 5 ngs, about 3 ngs or about 1 ng.

In some embodiments, a sample that is processed according to various methods disclosed herein includes a mixed nucleic acid population derived from one or more of whole blood, plasma, serum, urine, stool or saliva. In some embodiments, a mixed nucleic acid population can be derived from blood. In some embodiments, blood, e.g., whole blood can be further processed to provide plasma and/or serum from which a mixed nucleic acid population for a sample is prepared.

In some embodiments, the disclosed methods (as well as related compositions, kits and systems) are useful in detecting genetic changes in small amounts of whole blood, plasma, serum or other bodily fluid. For example, the amount of bodily fluid (e.g., whole blood, plasma, serum or saliva) that is used to prepare a mixed nucleic acid population of a sample can be in the range of about 0.1 to several milliliters (mls). In some embodiments, the amount of whole blood, plasma, serum or other bodily fluid that is used to prepare a mixed nucleic acid population is about 0.1 ml, about 0.25 ml, about 0.5 ml, about 0.75 ml, about 1 ml, about 1.5 ml, about 2 mls, about 2.5 mls, about 3 mls, about 3.5 mls, about 4 mls, about 4.5 mls, about 5 mls about 5.5 mls, about 6 mls, about 6.5 mls, about 7 mls, about 7.5 mls, about 8 mls, about 8.5 mls, about 9 mls, about 9.5 mls, or about 10 mls, or any intervening volumes of the foregoing.

In some embodiments where whole blood is used to provide a mixed nucleic acid population of a sample, the amount of blood is about or less than 0.1 ml, 0.25 ml, about 0.5 ml, about 0.75 ml, about 1 ml, about 1.5 ml, about 2 mls, about 2.5 mls or about 3 mls. In some embodiments, the amount of blood is no greater than about 0.25 ml, about 0.5 ml, about 0.75 ml, about 1 ml, about 1.5 ml, about 2 mls, about 2.5 mls or about 3 mls.

In some embodiments where plasma or serum is used to provide a mixed nucleic acid population of a sample, the amount of plasma or serum is about or less than 0.1 ml, 0.25 ml, about 0.5 ml, about 0.75 ml, about 1 ml, about 1.5 ml, about 2 mls, about 2.5 mls or about 3 mls. In some embodiments, the amount of plasma or serum is no greater than about 0.25 ml, about 0.5 ml, about 0.75 ml, about 1 ml, about 1.5 ml, about 2 mls, about 2.5 mls or about 3 mls.

Figure 1:
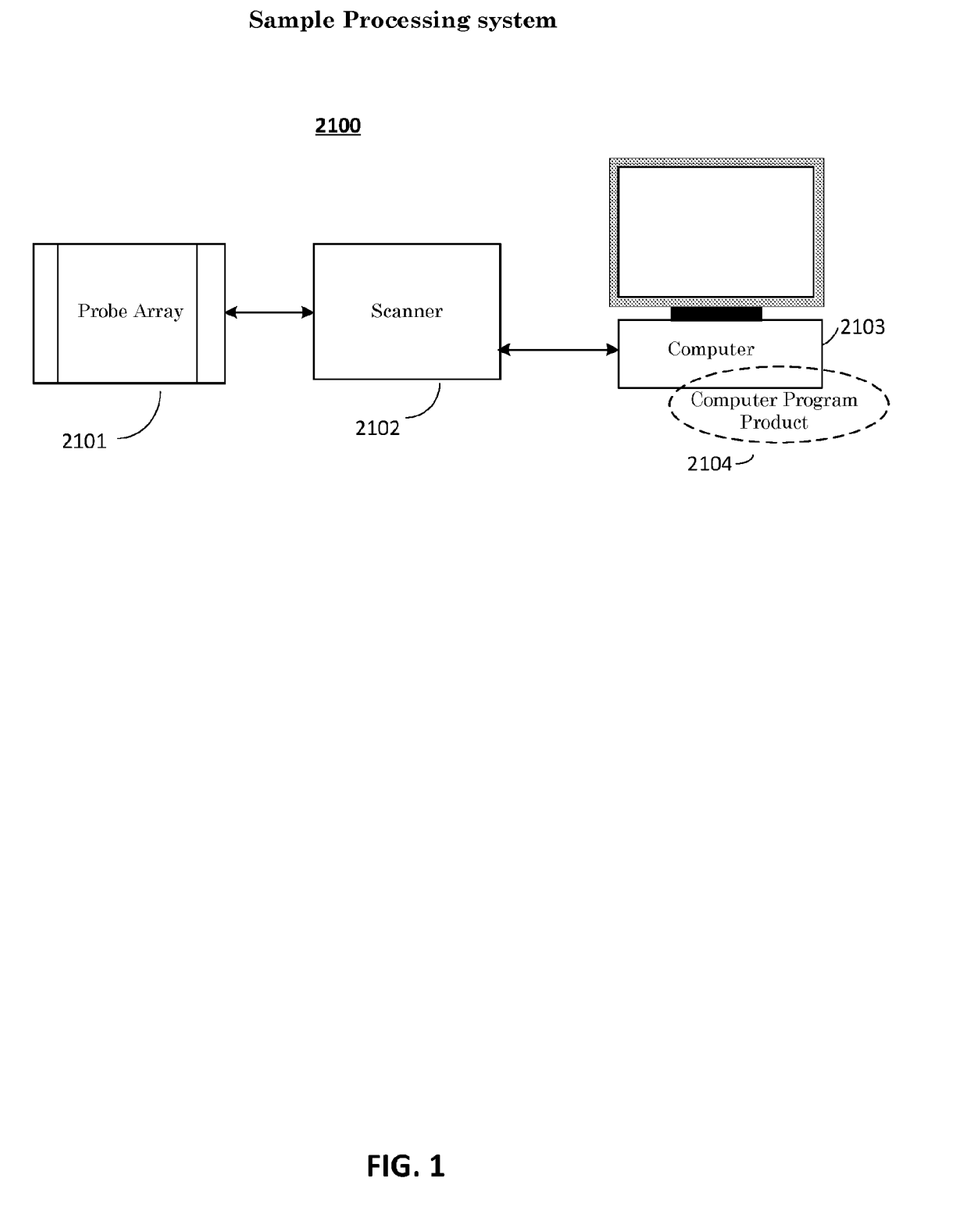
FIG. 1 illustrates a sample processing system in accordance with an embodiment of the present invention.

FIG. 1 illustrates a sample processing system 2100 in accordance with an embodiment of the present invention. The system includes an array containing probes specific for polymorphic loci in chromosomes of interest (e.g., chromosomes 13, 18, 21, X and Y) as well as representative reference chromosomes (e.g., chromosomes 1 and 5) that are assumed to be diploid. Different probes at different sites on the array are configured to selectively hybridize to allele-specific extension products that are generated prior to hybridization to the array, different allele-specific extension products will therefore hybridize to different sites on the array even though they differ by as little as one nucleotide. The hybridized allele-specific products are then treated in order to generate a detectable signal in proportion to the amount of hybridized product present. This-signal-generating treatment process is performed according to procedures outlined in the Axiom 2.0 Manual provided with the Axiom 2.0 reagent kit (catalog #901758). Signals emanating from the array were detected and analyzed as described in the following passages.

Sample processing system comprises probe array 2101, scanner 2102, and computer 2103 which is configurable by computer program 2104 to process data received from scanner 2102. Those skilled in the art will appreciate that various other components of a sample processing system such as system 2100 would be present but are not separately illustrated herein including, for example, a fluid handling system for handling various fluids (including, for example, biological samples to be placed in contact with probe array 2101, various washes, buffers, and other fluids), and an autoloader for handling and transport of one or more probe arrays such as probe array 2101 including positioning probe arrays for interaction with a fluid handling system and with scanner 2102.

In one embodiment, probe array 2101 is optimized for use in analyzing biological samples taken from a pregnant female. In a particular embodiment, probe array 2101 comprises probes for a plurality of polymorphic sites on one or more chromosomes, each polymorphic site associated with a single nucleotide polymorphism. In some embodiments, probe array 2101 comprises probes corresponding to: 10,867 or more unique SNPs on chromosomes 1 & 5; 7,559 or more unique SNPs on chromosome 13; 4,855 or more unique SNPs on chromosome 18; 2,083 or more unique SNPs on chromosome 21; 1,0661 unique SNPs on chromosome X; and 593 unique SNPs on chromosome Y. In one embodiment, the probe array includes approximately 2-50 or more replicate probes corresponding to each SNP. In some embodiments, where array space constraints limit the ability to have both a large number of probes and a large number of replicates, results are improved by having a smaller number of replicates (e.g., 2-6) so that a larger number of unique probes (for different polymorphic loci) can fit on an array of comparable size. One possible implementation (for illustrative purposes only) in which replicate numbers are relatively low (2 replicates for some probes and 6 replicates for others) and numbers of unique probes are relatively high for a given size probe array is shown in TABLE I below:

TABLE I

| Chrm | Number of unique probes with 2 replicates per unique probe | Number of unique probes with 6 replicates per unique probe | Total |
|---|---|---|---|
| 1 & 5 | 1,233 | 9,634 | 10,867 |
| 13 | 1,322 | 6,237 | 7,559 |
| 18 | 518 | 4,337 | 4,855 |
| 21 | 264 | 1,819 | 2,083 |
| X | 0 | 8,661 (+an additional 2000 with 4 replicates) | 10,661 |
| Y | 0 | 592 | 593 |

In alternative embodiments, the above numbers can be varied significantly without departing from an embodiment in which the number of unique probes is maximized relative to array space while still having some replicate probes on the array.

Figure 2:
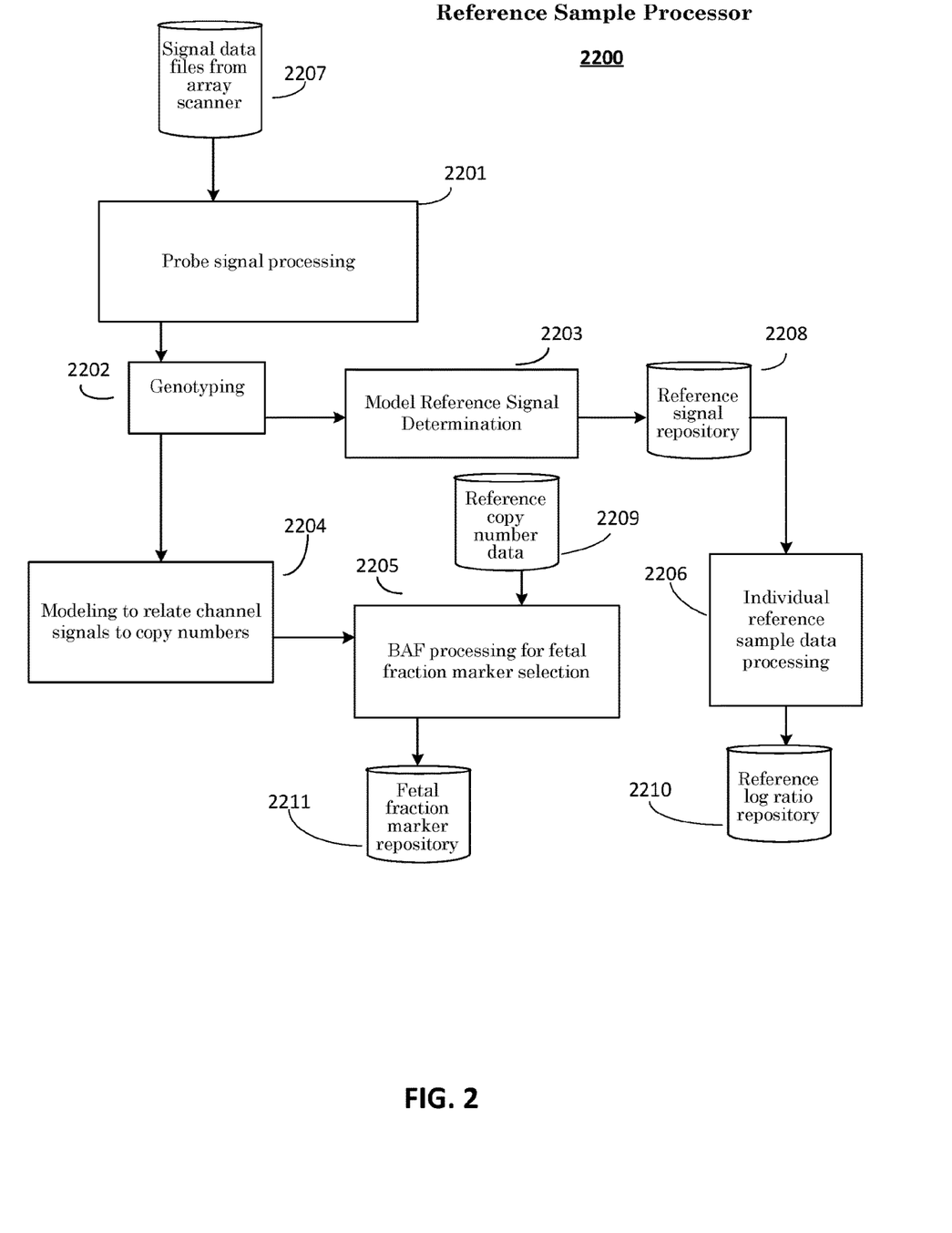
FIG. 2 illustrates a high-level block diagram of reference sample processor implemented by the system of FIG. 1 in accordance with an embodiment of the present invention.
Figure 3:
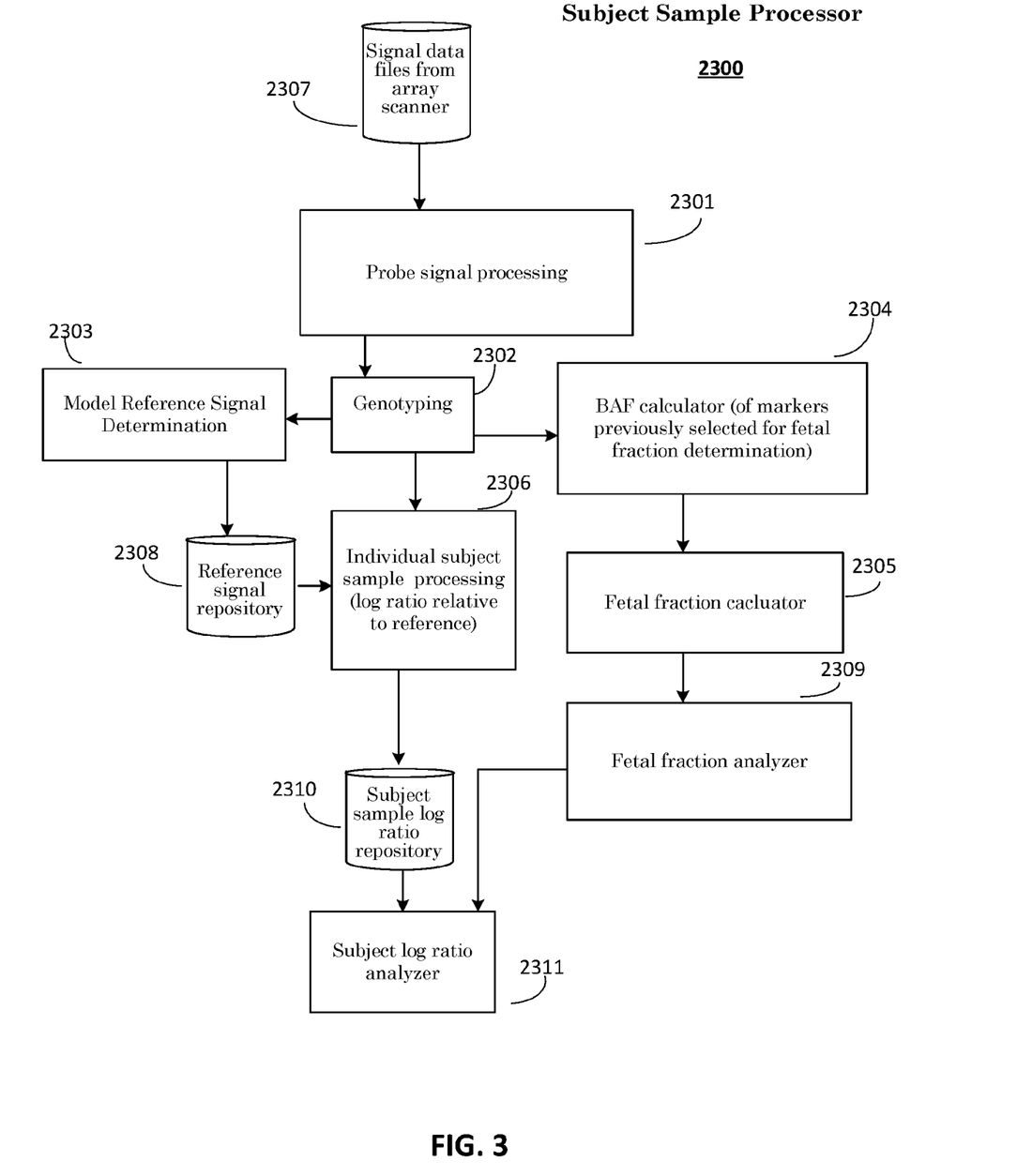
FIG. 3 illustrates a high-level block diagram of subject sample processor implemented by the system of FIG. 1 in accordance with an embodiment of the present invention.
Figure 4:
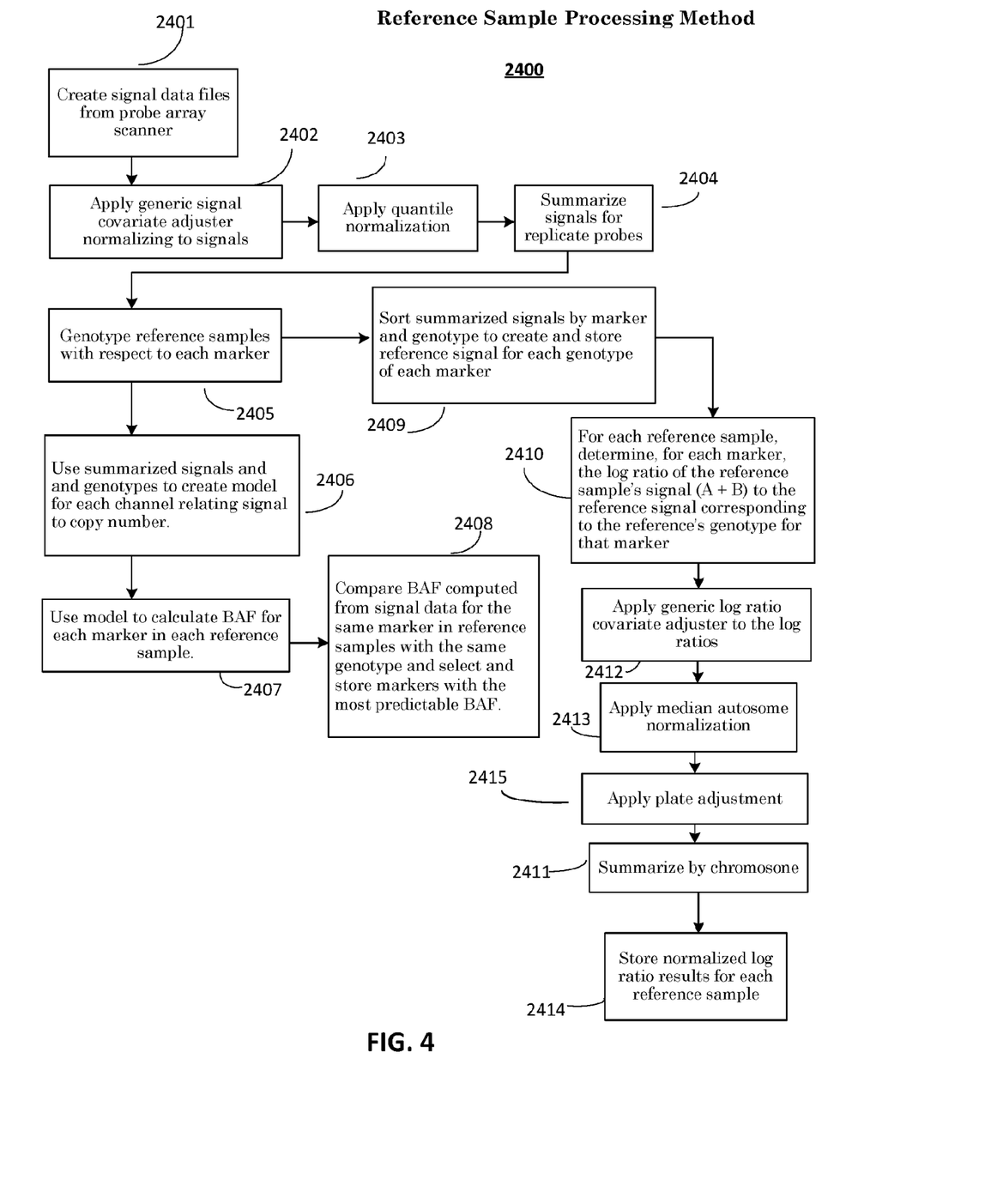
FIG. 4 illustrates a reference sample processing method in accordance with an embodiment of the present invention.
Figure 5:
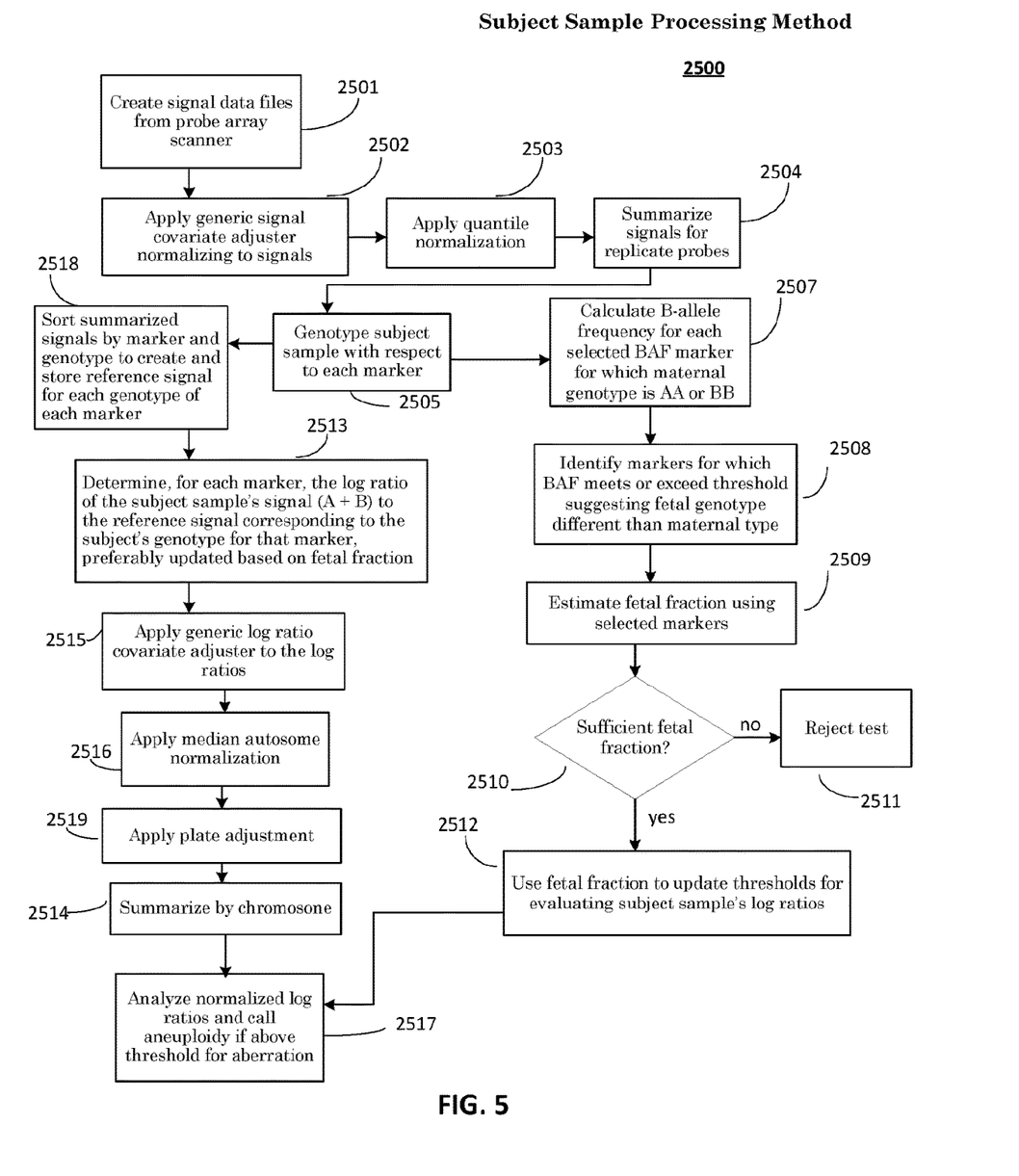
FIG. 5 illustrates a subject sample processing method in accordance with an embodiment of the present invention.

FIG. 2 and FIG. 3 illustrate block diagrams of reference and subject sample signal processing systems for implementing exemplary embodiments of the invention. FIG. 4 and FIG. 5 show detailed processing methods that, in accordance with exemplary embodiments of the invention, are carried out by the reference and subject signal processing systems of FIG. 2 and FIG. 3. The systems and methods of FIGS. 2-5 can be implemented on a computer such as computer 2103 of FIG. 1. In some alternative embodiments, those systems and methods can be implemented by a network of computers in communication with computer 2103. In such alternatives, all or part of a computer program product storing instructions for executing embodiments of the invention might be stored on remote network computers rather than on an end user computer.

FIG. 2 illustrates reference sample processor 2200. Processor 2200 includes various processing modules for processing signal data from reference samples in accordance with an embodiment of the invention. The particular elements shown in FIG. 2 are not necessarily all required in various alternative embodiments of the invention. Also, in alternatives, the particular elements and, in some cases, the arrangement of those elements, can be varied from that shown.

As will be discussed further in the context of other figures below, in some embodiments, portions of reference processor 2200 can be used for processing a plurality of subject samples wherein the subject samples are also used as reference samples. However, for clarity of illustration and explanation, reference processor 2200 is described in the context of processing reference samples only.

Data repository 2207 stores signal files generated from scanning probe arrays to which reference samples have been introduced and selectively hybridized. Probe signal processing module 2201 receives and processes signals received from repository 2207. Module 2201 normalizes and summarizes the signals as will be explained further in the context of FIGS. 4-5. Genotyping module 2202 uses the normalized and summarized signal values to perform genotyping to provide genotypes for each reference sample with respect to each SNP. Module 2203 creates model reference signals for each genotype of each SNP and stores them in reference signal repository (e.g., a data file) 2208.

Module 2204 uses genotyping data from module 2202 to create models relating signal values to copy numbers for each of two signal channels (as will be further described in the context of FIG. 4). Module 2205 computes B-allele frequency ("BAF") for each marker in each reference sample using the models generated by module 2204. Using the known reference copy number data retrieved from data repository 2209, BAF values corresponding to the same A and B allele copy numbers and same marker across reference samples are compared to each other and/or to the BAF value computed from the known copy number. Based on that comparison, module 2205 identifies the markers where B-allele frequencies computed from signals are most predictive of actual allele copy numbers and saves them in fetal fraction marker selection repository 2211. The identified markers are saved for later use in determining fetal fraction in subject maternal samples (e.g., pregnant female patient samples).

Module 2206 processes signals for individual reference samples individually to compute log ratios relative to the reference signals stored in repository 2208. Module 2206 stores the results in reference log ratio repository 2210.

FIG. 3 illustrates subject sample processor 2300. Processor 2300 includes various processing modules for processing signal data from subject (e.g., patient) samples in accordance with an embodiment of the invention. The particular elements shown in FIG. 3 are not necessarily all required in various alternative embodiments of the invention. Also, in alternatives, the particular elements and, in some cases, the arrangement of those elements, can be varied from that shown.

Data repository 2307 stores signal files generated from scanning probe arrays to which subject samples have been introduced and selectively hybridized. Probe signal processing module 2301 receives and processes signals received from repository 2307. Module 2301 carries out the same processing as module 2201 as will be explained further in the context of FIGS. 4-5. Genotyping module 2302 uses the normalized and summarized signal values received from module 2301 to perform genotyping to provide genotypes for each subject sample with respect to each SNP.

The illustrated embodiment includes module 2303 which uses signals from a plurality of subject samples processed on a same sample plate to create model reference signals for each genotype of each SNP and module 2303 stores them in reference signal repository (e.g., a data file) 2308. Note that, in some embodiments, model reference signals obtained from a prior reference assay have been previously determined by a reference processor such as processor 2200 illustrated in FIG. 2. In such alternatives, a subject sample processor such as processor 2300 would not necessarily require a separate model reference signal determination module such as module 2303 of FIG. 3. However, using subject samples to create model reference samples has the benefit of minimizing effects that might otherwise be attributable to the particular sample plate characteristics and/or assay conditions if the reference data is obtained from a different sample plate assayed at an earlier time.

Module 2304 uses genotyping data from module 2302 and marker-specific models from module 2204 relating A-signals to A-allele copy numbers and B-signals to B-allele copy numbers to convert A-signal values to A-copy numbers and B-signal values to B-copy numbers and then calculates the B-allele frequency (BAF) for each marker. As will be described in more detail in the context of FIG. 5, fetal fraction calculator 2305 calculates an estimated fetal fraction using the distribution of BAF values.

Fetal fraction analyzer 2309 determines whether the sample has sufficient fetal fraction to be used for evaluating aneuploidy. If so, then, fetal fraction analyzer 2309 uses the fetal fraction to update reference values for expected signals in view of the fetal fraction estimate, as will be further described in the context of FIG. 5.

Module 2306 processes an individual subject sample to obtain log ratios for a signal corresponding to each marker relative to an appropriate reference signal and stores the log ratios in repository 2310. Specifically, module 2306 uses a reference signal corresponding to the determined genotype of the major subpopulation (for example, the genotype of the maternal DNA) for that marker (as will be further described in the context of FIG. 5) to obtain a log ratio value for the subject's signal value for that marker relative to a reference value. In a preferred embodiment, the estimated fetal fraction is used to determine the expected signal threshold for an abnormal log ratio. However, in an alternative embodiment, a determined fetal fraction is not necessarily used to determine the expected signal for an abnormal log ratio; rather, anything not commensurate with a normal log ratio can be used.

Module 2311 analyzes the log ratio values to determine whether thresholds are met for calling aneuploidy.

FIG. 4 illustrates reference sample processing method 2400. In one embodiment, method 2400 is executed by reference processor 2200 of FIG. 2. The particular steps shown in FIG. 4 are not necessarily all required in various alternative embodiments of the invention. Also, in alternatives, the particular steps and, in some cases, the order, can be varied from that shown.

Step 2401 creates signal data files using signal data received from scanner 2102 (shown in FIG. 1). Scanner 2102 detects probe signals in two different channels for each marker, a first channel corresponding to the A-allele of that marker and a second channel corresponding to the B-allele of that marker. In this embodiment, probes are designed to be marker specific, but are detectable in different channels depending on which allele (A or B) of the marker the probe has hybridized to. Note that, in alternative embodiments, different probes for each allele of a marker may be used.

Steps 2402-2404 perform initial probe signal processing. Specifically, step 2402 applies generic signal covariate adjuster normalizing to the signals. In one embodiment, this processing normalizes the signals with respect to variables such as, for example, guanine and cytosine content (GC content) and probe fragment length. Step 2403 applies quantile normalization. Step 2404 summarizes replicate probe values. In one example, this comprises determining, for each marker with respect to each reference sample, a median signal value for all replicate probes hybridized to the A-allele (A-signal) and a median signal value for all replicate probes hybridized to the B-allele (B-signal).

Step 2405 genotypes each reference sample with respect to each marker. Step 2409 then creates a reference signal corresponding to each of the three possible genotypes of each marker as follows: For a first marker, a first reference sample's A-signal for that marker is added to the first reference sample's B-signal for that marker to obtain a combined A+B signal for the first marker with respect to the first reference. This is repeated for all other reference samples with respect to the first marker. Then, the median signal for the first marker across all references with a particular genotype is determined. For example, for marker1, the median signal value (A+B) for all references who have an AA genotype for that marker is stored as a reference signal. Similarly, for marker1, the median signal value (A+B) for all references who have a BB genotype for that marker is stored as a separate reference signal. And, for marker1, the median signal value (A+B) for all references who have an AB genotype is stored. This is repeated for each marker interrogated by the probe array. An example of normalized reference signals (A+B) determined in this manner for three different markers in chromosome 1 is shown below in Table II:

TABLE II

| Marker | Chrm | Median for AA genotype reference samples | Median for BB genotype reference samples | Median for AB genotype reference sample |
|---|---|---|---|---|
| tag002626 | 1 | 984.0628318 | 745.1495922 | 864.2744595 |
| tag002753 | 1 | 660.4613573 | 969.9901649 | 756.9943685 |
| tag002806 | 1 | 1128.81335 | 973.3259848 | 988.8751251 |

In some embodiments, log ratios can be calculated and further processed at steps 2410, 2412, 2413, 2415, and 2411 for each reference sample as follows. Step 2410, for each reference sample, determines a log ratio for each marker as a log ratio of the reference sample's signal for that marker to the appropriate median reference signal (e.g., such as those values in Table II above) depending on whether the reference sample has been genotyped as AA, BB, or AB for that marker. Step 2412 applies generic log ratio covariate normalizing to the log ratios. Step 2413 optionally applies median autosome normalization on a per sample basis. Specifically, if the median of the median log ratios across all chromosomes is not 0 for a given sample, then all values are adjusted by the increment needed to make the median of medians 0. Step 2415 optionally applies a plate adjustment by applying median autosome normalization again, but this time across all samples on the plate, applying an appropriate incremental adjustment as needed to make the median of medians 0. Step 2411 summarizes each reference sample by chromosome or by some other unit of interest. In one embodiment, this unit can be a chromosome arm, or a smaller or longer region of interest. In one embodiment, this is done by taking the median of all log ratios for all markers on a given chromosome as the summarized value for that chromosome for a given sample. In alternative embodiments, an average or other methods of summarizing might be used. Step 2414 stores normalized log ratios results for each reference sample.

Steps 2406-2408 are used to select particular markers that are preferred for use in determining fetal fraction of a subject sample. Markers for which a good ability to predict B-allele frequency for at least one of the homozygous genotypes is demonstrated are selected.

Step 2406 uses summarized signals from step 2404 and genotypes from step 2405 to create a model relating signal value to copy number for each allele of each marker. In one embodiment, the model is a linear model. In another embodiment the model is non-linear such as, for example, a Langmuir model. One method for creating a linear model is now described in further detail. However, the described method can of course be varied in alternative embodiments.

In one embodiment, two models, an A-model and a B-model, are created for all autosomal markers where each of the three possible genotypes is represented by at least two reference samples. The A-model relates A-signal value to A-copy number and the B-model relates B-signal value to B-copy number. First, reference sample's genotype of the marker is converted to an "A copy number" and "B copy number" according to Table III:

TABLE III

| Genotype | A copy number | B copy number |
|---|---|---|
| AA | 2 | 0 |
| AB | 1 | 1 |
| BB | 0 | 2 |

Then, weighted linear regression is separately performed on (i) all the A signal values (versus A copy number) for all reference samples for the marker and (ii) all B signal values (versus B copy number) for all the reference samples for the marker. In one embodiment, weights are applied based on a predicted standard deviation for each copy number. The predicted standard deviation is determined from conducting linear regression on the observed standard deviations for the observed reference signals. The resulting predicted standard deviation for copy number CNi (where i=0, 1, or 2) is noted herein by "$pSD_{CNi}$". Then, when performing weighted linear regression on the observed signal values versus copy number, the observed value is weighted by multiplying it by $1/(pSD_{CNi})^2$ where $pSD_{CNi}$ is the predicted standard deviation corresponding to the copy number associated with the reference sample's genotype for the marker.

The above-referenced weighted linear regression is used on the A-signal values and corresponding A copy numbers to generate the Aintercept and Aslope parameter values for the following A-model equation:

Asignal=Aintercept+Aslope*Acopynumber

And, the above-referenced weighted linear regression is used on the B-signal values and corresponding B copy numbers to generate the Bintercept and Bslope parameter values for the following B-model equation:

Bsignal=Bintercept+Bslope*Bcopynumber.

Using the above referenced A-model and B-model equations, step 2407 predicts the A copy number (pAcopynumber) and B copy number (pBcopynumber) for an individual reference sample based on, respectively, the A signal value and B signal value (note, the A signal is a summarized signal using the median value of A signals for all replicate probes and the B signal is a summarized signal using the median value of B signals for all replicate probes) for a particular marker. Therefore, pAcopynumber=(Asignal−Aintercept)/Aslope and pBcopynumber=(Bsignal−Bintercept)/Bslope. Using the predicted copy number, the BAF is computed for each marker in each reference sample as follows:

pBcopynumber/(pAcopynumber+pBcopynumber).

Step 2407 computes BAFs (based on the model from 2406) for known copy number information from reference samples for each marker with sufficient reference information. Then, in step 2408, computed BAFs for the same marker and genotype are compared to each other. Based on this comparison, markers for which the computed BAFs for AA genotypes have the lowest standard deviation are selected for AA BAFs and markers for which the computed BAFs for BB genotypes have the lowest standard deviation are selected for BB BAFs. Selection is done for later use in estimating fetal fraction based on signals from subject samples.

FIG. 5 illustrates subject sample processing method 2500. In one embodiment, method 2500 is executed by subject sample processor 2300 of FIG. 3. The particular steps shown in FIG. 4 are not necessarily all required in various alternative embodiments of the invention. Also, in alternatives, the particular steps and, in some cases, the order, can be varied from that shown.

Steps 2501, 2502, 2503, 2504, and 2505 are substantially identical to steps 2401, 2402, 2403, 2404, and 2405 of method 2400 of FIG. 4 and won't be described in detail again here except to note that the steps in the context of method 2500 are performed on data files obtained from scanning subject (e.g. patient) samples obtained from pregnant females. Similar to step 2404, the results of step 2504 are summarized A-channel signals (e.g. median signal value) for all replicate probes hybridized to an A-allele for each marker for each subject sample (A-signals) and summarized B-channel signals (e.g. median signal value) for all replicate probes hybridized to a B-allele for each marker for each subject sample (B-signals).

Step 2505, like step 2405, obtains genotypes for each subject sample with respect to each marker. Although a sample from a pregnant female presumably includes a fetal fraction, step 2505 determines an apparent genotype of the mother or the genotype of the major subpopulation.

In some embodiments, several different subject maternal samples processed on a same sample plate can be used to create reference signals for subsequent log ratio calculations. In such embodiments, step 2518 sorts the summarized signals for all subject samples by genotype to determine reference signals in the same manner as previously described step 2409 in FIG. 4. The only difference is that step 2518 uses current subject samples on a current sample plate to determine genotype-specific reference signals. However, in alternative embodiments that do not include step 2518, genotype-specific reference signals established for a set of reference samples previously analyzed on a different sample plate (e.g., as established by step 2409 of FIG. 4) can be used instead.

Step 2507 calculates a B-allele frequency (BAF) for markers identified in step 2408 of FIG. 4 for which the maternal genotype of the subject sample, as determined in step 2505 of FIG. 5 is AA or BB. Prior to calculating BAF, step 2507 converts A-signal values to predicted A copy numbers and B-signal values to predicted B copy numbers in the same manner described in the context of step 2407 of FIG. 4, i.e., using reference models such as the models determined at step 2406 of FIG. 4.

Step 2508 identifies markers for which the calculated BAF value meets or exceeds a threshold suggesting a fetal genotype of AB (i.e., different than mother's genotype, which is either AA or BB for each marker used in step 2508). In one embodiment, when the maternal genotype is AA for the marker, a BAF between about 0.015 and 0.2 suggests a fetal genotype that is different than AA and triggers selection of the marker for use in determining fetal fraction. Also, in such an embodiment, when the maternal genotype is BB for the marker, a BAF between about 0.8 and 0.985 suggests a fetal genotype that is different than BB and triggers selection of the marker for use in determining fetal fraction. However, in alternative embodiments, these ranges might be varied or different ranges might be used for different markers without necessarily departing from the scope of this aspect of the present invention.

Step 2509 estimates fetal fraction using the selected markers. Specifically, in one embodiment, fetal fraction is estimated for the selected markers as follows. For markers in which the mother's genotype is AA, a fetal fraction $\alpha$ is estimated based on the equation BAF=$\alpha/2$, i.e., $\alpha=2*$BAF. The basis for this equation is the following: If the mother is AA and the fetus is AB, Bcopynumber=$\alpha$ and Acopynumber=$2*(1-\alpha)+\alpha=2-\alpha$. Therefore, Acopynumber+Bcopynumber=$2-\alpha+\alpha=2$. In a similar manner, if the mother's genotype is BB, a fetal fraction $\beta$ is estimated based on the equation BAF=$1-\beta/2$. The basis for this equation is the following: If the mother is BB and the fetus is AB, Bcopynumber=$2(1-\beta)+\beta=2-\beta$ and AcopyNumber=$\beta$. Therefore, Acopynumber+Bcopynumber=2, and BAF=$(2-\beta)/2=1-\beta/2$.

Step 2510 determines whether the fetal fraction determined in step 2509 is sufficiently high and/or sufficiently reliable for using the subject's sample to screen for aneuploidy. In one embodiment, step 2510 determines fetal faction sufficiency/reliability in two stages as follows: First, it is determined if a sufficiently high enough fraction of markers for which the mother's genotype is AA has an $\alpha \geq 3\%$ AND whether a sufficiently high enough fraction of markers for which the mother's genotype is BB has $\beta \geq 3\%$. The use of a 3% threshold might vary based on the noisiness of the particular assay utilized. However, in one embodiment, it is assumed the noise level is such that some markers that are AA (or BB) in both mother and fetus will show BAFs corresponding to a fetal fraction of more than 3%. Regarding the percentage of markers that must meet the 3% threshold, in one embodiment, if less than 20% of the markers for which the mother is AA have $\alpha \geq 3\%$ or if less than 9% of the markers for which the mother's genotype is AA have $\beta \geq 3\%$, then the test is rejected. The respective thresholds of 20% and 9% may be varied in alternative embodiments. In general, these are empirically determined thresholds intended to optimize specificity and sensitivity, and they may be varied to favor either of these performance measures, depending, in some cases, on assay noisiness.

If the sample passes the reliability thresholds such as, for example, those referenced above, the median $\alpha$ and median $\beta$ across the relevant markers are, in one embodiment, used to estimate fetal fraction. Optionally, an additional reliability threshold is applied and the sample is rejected if $\alpha$ and $\beta$ are not within a specified number of percentage points of each other for the sample to be accepted. In one embodiment, the specified number of percentage points is 2-3% (e.g., if $\alpha=4\%$ and $\beta=8\%$, the estimate is considered insufficiently reliable). However, in some embodiments, this additional reliability threshold is not applied. Once $\alpha$ and $\beta$ are established and considered acceptable, the sample is rejected if the values of $\alpha$ and $\beta$ (for example, an average, or a weighted average) indicate a fetal fraction of less than 4%.

If the result of step 2510 is no, then step 2511 rejects the sample. Presumably, in most cases, another sample can be taken from the pregnant female for retesting, if desired, at a later date. In some alternative embodiments, any rejection of a subject sample based on the various criteria reference above for reliability and/or sufficiency rejection is only conditional and a conditionally rejected sample is still potentially considered if the relevant log ratios analyzed at step 2517 (discussed further below) are sufficiently extreme to clearly indicate aneuploidy.

If the result of step 2510 is yes, then, preferably, step 2512 uses the estimated fetal fraction to update the thresholds used for the log ratio. Step 2513 selects an appropriate reference signal based on the determined maternal genotype for the marker (e.g., for a particular marker, selects one of the three reference signals shown in Table III above corresponding to the maternal genotype) and determines a log ratio of the subject sample's signal for the relevant marker (summarized A signal+summarized B signal) to the relevant selected reference signal.

Further processing is carried out in steps 2515, 2516, 2519, and 2514 similar to that already describe above in the context of, respectively, steps 2412, 2413, 2415, and 2411 of FIG. 4.

Step 2517 analyzes the resulting normalized log ratios and calls aneuploidy if the ratios are above a threshold indicating an aberration. The theoretical log ratio for a normal sample is 0, while for a trisomy sample with 5% fetal fraction it is Log 2((2*0.95+3*0.05)/2)=0.03562. However, in a particular implemented embodiment, an attenuation factor can be determined empirically and considered. For example, in an embodiment with an attenuation factor of 0.8, a predicted log ratio for fetal trisomy when the fetal fraction is 5% is 0.8*0.03562. In one such embodiment (i.e., with a 5% fetal faction, and an assay-related attenuation of 0.8, a threshold log ratio for calling aneuploidy might be between 0.02 and 0.03. However, alternative embodiments can use other thresholds or other methods to compute attenuation.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of the methods in FIG. 4, and FIG. 5 and alternative embodiments may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
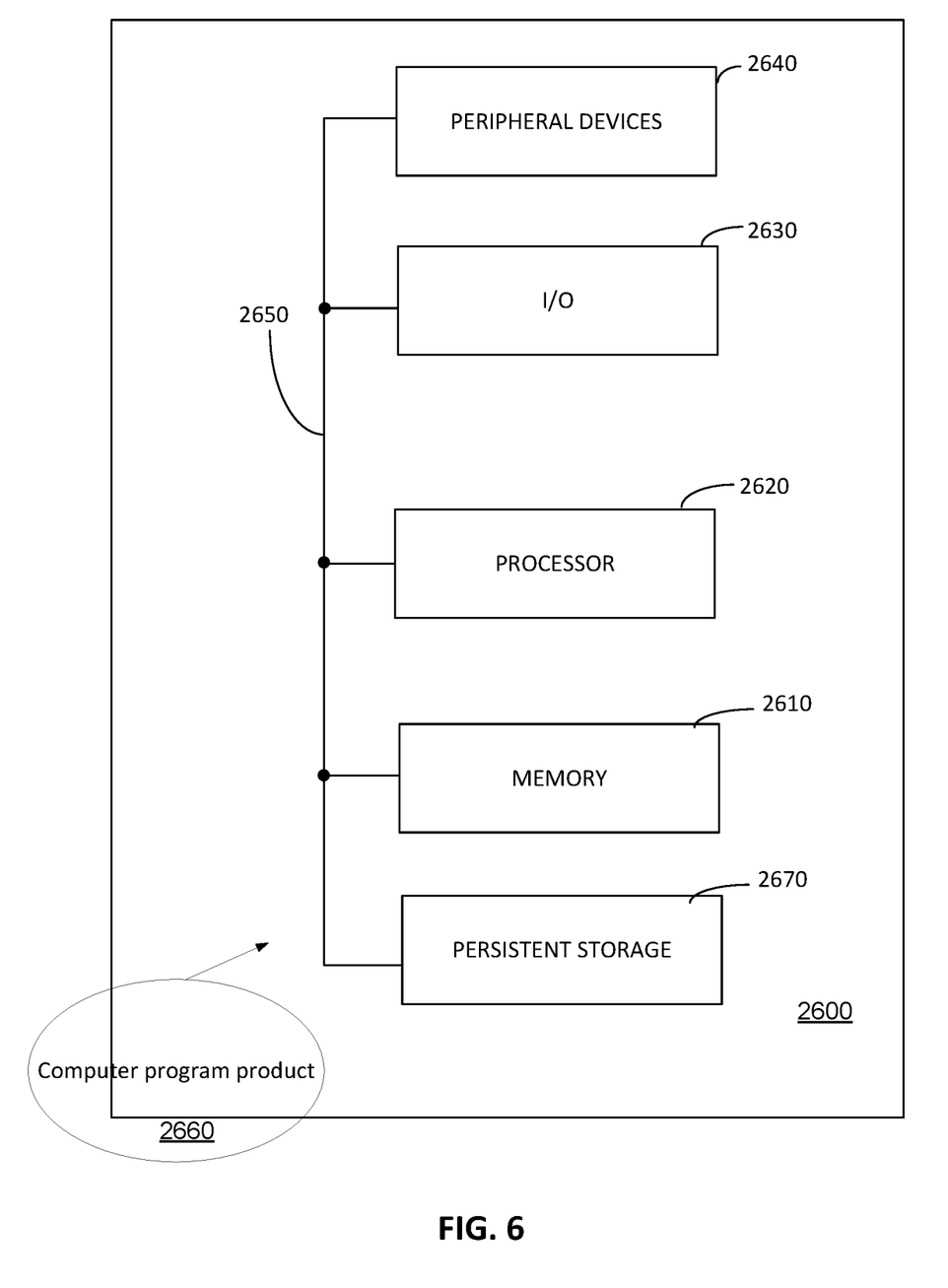
FIG. 6 illustrates an exemplary computer system configurable by a computer program product to carry out embodiments of the present invention.

FIG. 6 shows an example of a computer system 2600, one or more of which may provide one or more of the components of, or alternatives to computer 2103 of FIG. 1. Computer system 2600 executes instruction code contained in a computer program product 2660 (which may, for example, be the computer program product 2104 of the embodiment of FIG. 1.) Computer program product 2660 comprises executable code in an electronically readable medium that may instruct one or more computers such as computer system 2600 to perform processing that accomplishes the exemplary method steps performed by the embodiments referenced herein. The electronically readable medium may be any non-transitory medium that stores information electronically and may be accessed locally or remotely, for example via a network connection. In alternative embodiments, the medium may be transitory. The medium may include a plurality of geographically dispersed media each configured to store different parts of the executable code at different locations and/or at different times. The executable instruction code in an electronically readable medium directs the illustrated computer system 2600 to carry out various exemplary tasks described herein. The executable code for directing the carrying out of tasks described herein would be typically realized in software. However, it will be appreciated by those skilled in the art, that computers or other electronic devices might utilize code realized in hardware to perform many or all the identified tasks without departing from the present invention. Those skilled in the art will understand that many variations on executable code may be found that implement exemplary methods within the spirit and the scope of the present invention.

The code or a copy of the code contained in computer program product 2660 may reside in one or more storage persistent media (not separately shown) communicatively coupled to system 2600 for loading and storage in persistent storage device 2670 and/or memory 2610 for execution by processor 2620. Computer system 2600 also includes I/O subsystem 2630 and peripheral devices 2640. I/O subsystem 2630, peripheral devices 2640, processor 2620, memory 2610, and persistent storage device 2670 are coupled via bus 2650. Like persistent storage device 2670 and any other persistent storage that might contain computer program product 2660, memory 2610 is a non-transitory media (even if implemented as a typical volatile computer memory device). Moreover, those skilled in the art will appreciate that in addition to storing computer program product 2660 for carrying out processing described herein, memory 2610 and/or persistent storage device 2670 may be configured to store the various data elements referenced and illustrated herein.

Those skilled in the art will appreciate computer system 2600 illustrates just one example of a system in which a computer program product in accordance with an embodiment of the present invention may be implemented. To cite but one example of an alternative embodiment, execution of instructions contained in a computer program product in accordance with an embodiment of the present invention may be distributed over multiple computers, such as, for example, over the computers of a distributed computing network.

While the present invention has been particularly described with respect to the illustrated embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the underlying principles of the invention as described by the various embodiments reference above and below.

What is claimed is:

1. A method for analyzing a biological sample, comprising:
    obtaining the biological sample from a subject who is a pregnant female, the biological sample including nucleic acid of both maternal and fetal origin and containing a target nucleic acid sequence located on a target chromosome, the target nucleic acid sequence containing a polymorphic site for a single nucleotide polymorphism (SNP), the SNP being associated with a first allelic variant ("A allele") and a second allelic variant ("B allele"), wherein the polymorphic site of the SNP can be homozygous for the A allele ("AA"), homozygous for the B allele ("BB") or heterozygous ("AB");
    generating a population of nucleic acid fragments containing or derived from the target nucleic acid sequence;
    conducting a first assay comprising:
        (a) contacting the population of nucleic acid fragments with an oligonucleotide array containing a plurality of first oligonucleotide probes configured to hybridize to the first allelic variant of the target nucleic acid sequence containing the polymorphic site of the SNP and a plurality of second oligonucleotide probes configured to hybridize to the second allelic variant of the target nucleic acid sequence containing the polymorphic site of the SNP; and (b) detecting, using a detector, first signals indicating hybridization of one or more of the first oligonucleotide probes to one or more nucleic acid fragments of the population containing the first allelic variant of the SNP and second signals indicating hybridization of one or more of the second oligonucleotide probes to one or more nucleic acid fragments of the population containing the second allelic variant of the SNP, wherein the detector has a first and a second detection channel, and the method includes detecting the first signals in the first channel and the second signals in the second channel, wherein the first signals in the first channel indicate the amount of A allele present in the nucleic acid population and the second signals indicate the amount of B allele present in the nucleic acid population; and determining the copy number of the target chromosome in the fetus by determining a ratio of a first value to a second value.

2. The method of claim 1, further comprising calculating the observed B-allele frequency (BAF) for the allelic variants of the SNP present in the sample.

3. The method of claim 2, further including calculating the fetal fraction of the sample using the BAF.

4. The method of claim 1, further comprising calculating the first value by normalizing and summarizing the first signals to obtain a first normalized and summarized signal value, normalizing the second signals to obtain a normalized and summarized second signal value, and adding the normalized and summarized first signal value to normalized and summarized second signal value to obtain the first value.

5. The method of claim 1, further including determining a first maternal SNP genotype.

6. The method of claim 4, wherein the second value is obtained by:
conducting the first assay on additional biological samples serving as reference samples and identifying reference samples having an SNP genotype corresponding to the first maternal SNP genotype;
from conducting the first assay on the reference samples, obtaining first signals reference signals detected in the first channel indicating an amount of A allele present in the polymorphic site of the SNP with respect to the additional biological samples and obtaining second reference signals indicating the amount of B allele present at the polymorphic site.

7. The method of claim 6, wherein the additional biological samples are from non-pregnant individuals.

8. The method of claim 6, wherein the additional biological samples include some samples from pregnant females and some samples from non-pregnant individuals.

9. The method of claim 6, wherein the additional biological samples include samples from pregnant females assayed on the same oligonucleotide array as the biological sample from the subject pregnant female.

10. The method of claim 1, wherein the nucleic acid sample includes maternal blood, plasma or serum and the nucleic acid of both maternal and fetal origin includes cell-free DNA (cfDNA).

11. The method of claim 1, wherein the fetal DNA is no greater than 30% of total DNA in the nucleic acid sample.

12. The method of claim 1, wherein the fetal DNA is no greater than 20% of total DNA in the nucleic acid sample.

13. The method of claim 1, wherein the fetal DNA is no greater than 15% of total DNA in the nucleic acid sample.

14. The method of claim 1, wherein the fetal DNA is no greater than 10% of total DNA in the nucleic acid sample.

15. The method of claim 1, wherein the fetal DNA is no greater than 5% of total DNA in the nucleic acid sample.

16. The method of claim 1, wherein the fetal DNA is no greater than 15% and no less than 1% of total cell free DNA in the nucleic acid sample.

\* \* \* \* \*